US011883622B2

(12) United States Patent
Ross et al.

(10) Patent No.: US 11,883,622 B2
(45) Date of Patent: Jan. 30, 2024

(54) TRANSDERMAL DRUG DELIVERY DEVICE

(71) Applicant: SORRENTO THERAPEUTICS, INC., San Diego, CA (US)

(72) Inventors: Russell F. Ross, Jacksonville Beach, FL (US); Luke Hagan, Seattle, WA (US); Alexander Malkin, Pittsburgh, PA (US); Derek Hatchett, Brookline, MA (US); Jacob Marks, Mansfield, MA (US); Thomas Lutzow, Providence, RI (US)

(73) Assignee: SORRENTO THERAPEUTICS, INC., San Diego, CA (US)

( * ) Notice: Subject to any disclaimer, the term of this patent is extended or adjusted under 35 U.S.C. 154(b) by 355 days.

(21) Appl. No.: 17/178,817

(22) Filed: Feb. 18, 2021

(65) Prior Publication Data
US 2021/0170153 A1 Jun. 10, 2021

Related U.S. Application Data

(63) Continuation of application No. 16/224,249, filed on Dec. 18, 2018, now Pat. No. 10,953,211, which is a
(Continued)

(51) Int. Cl.
*A61M 37/00* (2006.01)
*A61M 5/42* (2006.01)
*A61M 5/158* (2006.01)

(52) U.S. Cl.
CPC ........ *A61M 37/0015* (2013.01); *A61M 5/158* (2013.01); *A61M 5/42* (2013.01);
(Continued)

(58) Field of Classification Search
CPC .... A61M 37/0015; A61M 5/158; A61M 5/42; A61M 5/425; A61M 2005/1587;
(Continued)

(56) References Cited

U.S. PATENT DOCUMENTS 5,250,023 A  10/1993  Lee et al.
5,279,544 A   1/1994  Gross et al.
(Continued)

FOREIGN PATENT DOCUMENTS

CN   201216811 Y    4/2009
EP     1471953 A2  11/2004
(Continued)

OTHER PUBLICATIONS

Office Action Report in Brazilian Patent Application No. BR 11 2015 020328 0 dated Oct. 13, 2021, 4 pages.
(Continued)

*Primary Examiner* — James D Ponton
(74) *Attorney, Agent, or Firm* — BAKER BOTTS L.L.P.

(57) ABSTRACT

A transdermal drug delivery device is disclosed that may comprise a housing including an upper housing portion and a lower housing portion. The lower housing portion may define a bottom surface including skin attachment means for releasably attaching the lower housing portion to skin of a user. The upper housing portion may at least partially surround a central region of the device. The device may also include a microneedle assembly and a reservoir disposed within the central region. The reservoir may be in fluid communication with the microneedle assembly. Additionally, the device may include a pushing element disposed above the microneedle assembly within the central region. The pushing element may be configured to provide a continuous bilateral force having a downward component transmitted through the microneedle assembly and an upward component transmitted through the skin attachment means.

18 Claims, 10 Drawing Sheets

Related U.S. Application Data continuation of application No. 14/762,844, filed as application No. PCT/IB2014/059345 on Feb. 28, 2014, now Pat. No. 10,183,156.

(60) Provisional application No. 61/770,639, filed on Feb. 28, 2013.

(52) U.S. Cl.
CPC ..... *A61M 5/425* (2013.01); *A61M 2005/1587* (2013.01); *A61M 2037/0023* (2013.01); *A61M 2037/0061* (2013.01)

(58) Field of Classification Search
CPC .. A61M 2037/0023; A61M 2037/0061; A61M 5/14248; A61M 2005/14252; A61M 2037/0046; A61M 5/00; A61M 5/14; A61M 5/142; A61M 5/14244
See application file for complete search history.

(56) References Cited

U.S. PATENT DOCUMENTS

| | | | |
|---|---|---|---|
| 5,527,288 A | 6/1996 | Gross et al. | |
| 5,800,420 A | 9/1998 | Gross et al. | |
| 5,848,991 A | 12/1998 | Gross et al. | |
| 5,957,895 A | 9/1999 | Sage et al. | |
| 6,074,369 A | 6/2000 | Sage et al. | |
| 6,186,982 B1 | 2/2001 | Gross et al. | |
| 6,375,978 B1 | 4/2002 | Kleiner et al. | |
| 6,623,457 B1 | 9/2003 | Rosenberg | |
| 6,656,147 B1 | 12/2003 | Gertsek et al. | |
| 6,780,171 B2 | 8/2004 | Gabel et al. | |
| 6,960,193 B2 | 11/2005 | Rosenberg | |
| 7,047,070 B2 | 5/2006 | Wilkinson et al. | |
| 7,115,108 B2 | 10/2006 | Wilkinson et al. | |
| 7,537,590 B2 | 5/2009 | Santini, Jr. et al. | |
| 7,611,481 B2 | 11/2009 | Cleary et al. | |
| 7,699,802 B2 | 4/2010 | Steinway et al. | |
| 7,828,771 B2 | 11/2010 | Chiang et al. | |
| 7,858,112 B2 | 12/2010 | Hatanaka et al. | |
| 7,896,837 B2 | 3/2011 | Wilkinson et al. | |
| 7,911,480 B2 | 3/2011 | Cleary et al. | |
| 8,029,469 B2 | 10/2011 | Ethelfeld | |
| 8,062,253 B2 | 11/2011 | Nielsen et al. | |
| 8,328,757 B2 | 12/2012 | Beebe et al. | |
| 2003/0014014 A1 | 1/2003 | Nitzan | |
| 2003/0050602 A1 | 3/2003 | Pettis et al. | |
| 2004/0106904 A1 | 6/2004 | Gonnelli et al. | |
| 2006/0036209 A1 | 2/2006 | Subramony et al. | |
| 2007/0224253 A1 | 9/2007 | Franklin | |
| 2007/0250018 A1 | 10/2007 | Adachi et al. | |
| 2008/0183144 A1 | 7/2008 | Trautman et al. | |
| 2009/0030365 A1 | 1/2009 | Tokumoto et al. | |
| 2009/0042970 A1 | 2/2009 | Herschkowitz et al. | |
| 2009/0118672 A1 | 5/2009 | Gonnelli et al. | |
| 2010/0121307 A1 | 5/2010 | Lockard et al. | |
| 2010/0179473 A1 | 7/2010 | Genosar | |
| 2010/0209483 A1 | 8/2010 | Franklin | |
| 2011/0022002 A1 | 1/2011 | Hanson et al. | |
| 2011/0097393 A1 | 4/2011 | Al-Ghananeem | |
| 2011/0172601 A1* | 7/2011 | Beebe ............... | A61M 37/0015 604/173 |
| 2011/0172609 A1 | 7/2011 | Moga et al. | |
| 2011/0172637 A1 | 7/2011 | Moga et al. | |
| 2011/0172638 A1 | 7/2011 | Moga et al. | |
| 2011/0172645 A1 | 7/2011 | Moga et al. | |
| 2011/0276027 A1 | 11/2011 | Trautman et al. | |
| 2011/0276028 A1 | 11/2011 | Singh et al. | |
| 2011/0288526 A1 | 11/2011 | Wei | |
| 2012/0109065 A1 | 5/2012 | Backes | |
| 2012/0109066 A1 | 5/2012 | Chase et al. | |
| 2012/0109067 A1 | 5/2012 | Ozawa et al. | |

FOREIGN PATENT DOCUMENTS

| | | |
|---|---|---|
| EP | 1682203 A2 | 7/2006 |
| JP | 2010516337 A | 5/2010 |
| WO | 0062908 A1 | 10/2000 |
| WO | 03024508 A2 | 3/2003 |
| WO | 2005039673 A2 | 5/2005 |
| WO | 2008007906 A1 | 1/2008 |
| WO | 2008091602 A2 | 7/2008 |

OTHER PUBLICATIONS

China Second Office Action for Patent Application CN 201910125304.3 dated Jun. 11, 2021; 32 pp.
EP Search Report for European Patent Application 14757306.7 dated Mar. 6, 2017; 12 pp.
JPO Office Action for JP Patent Application 2015-559599 dated Dec. 5, 2017; 7 pp.
CN First Office Action for CN Patent Application 201910125304.3 dated Nov. 20, 2020; 30 pp.
JPO Office Action for JP Patent Application 2019-082664; dated Apr. 14, 2020; 10 pages.
IN Examination Report for IN Patent Application 8390/DELNP/2015 dated Oct. 26, 2020; 7 pp.

* cited by examiner

TRANSDERMAL DRUG DELIVERY DEVICE

CROSS-REFERENCE TO RELATED APPLICATION

This application claims the benefit of U.S. patent application Ser. No. 16/224,249, filed on Dec. 18, 2018, the entire contents of which are incorporated herein by reference. U.S. patent application Ser. No. 16/224,249 is a continuation of U.S. patent application Ser. No. 14/762,844, now U.S. Pat. No. 10,183,156, filed on Jul. 23, 2015, the entire contents of which are incorporated herein by reference. U.S. patent application Ser. No. 14/762,844 is the U.S. national stage application of International Application No. PCT/M2014/059345, filed on Feb. 28, 2014, the entire contents of which are incorporated herein by reference. International Application No. PCT/IB2014/059345 claims priority to U.S. Provisional Patent Application No. 61/770,639, filed on Feb. 28, 2013, the entire contents of which are incorporated herein by reference.

FIELD OF THE INVENTION

The present subject matter relates generally to devices for delivering drug formulations to a patient through the skin utilizing a microneedle assembly.

BACKGROUND OF THE INVENTION

Numerous devices have previously been developed for the transdermal delivery of drugs and other medicinal compounds utilizing microneedle assemblies. Microneedles have the advantage of causing less pain to the patient as compared to larger conventional needles. In addition, conventional subcutaneous (often intra-muscular) delivery of drugs via a needle acts to deliver large amounts of a drug at one time, thereby often creating a spike in the bioavailability of the drug. For drugs with certain metabolic profiles this is not a significant problem. However, many drugs benefit from having a steady state concentration in the patient's blood stream, a well-known example of such a drug is insulin. Transdermal drug delivery devices are technically capable of slowly administering drugs at a constant rate over an extended period of time. Thus, transdermal drug delivery devices offer several advantages relative to conventional subcutaneous drug delivery methods.

However, existing transdermal drug delivery devices often fail to consistently deliver all of the drug beneath the stratum corneum layer of the skin so that it can be absorbed into the body. In this regard, due to the small size of the needles, often times all or a portion of the drug is delivered only onto the top of the skin or into the stratum corneum layer where the drug cannot be absorbed into the body of the patient. This can happen for various reasons. For example, the needle depth may slightly retract from the desired insertion depth such as due to the inconsistent application of force on the needles or the natural elasticity of the skin acts to push the needles outwardly after insertion. Further complicating transdermal delivery with such small needles is that the skin may form such a complete juncture with the needle that the drug flows upwardly along the needle towards the point of insertion and away from the cellular layers capable of absorbing the drug into the body.

Accordingly, there remains a need for a transdermal drug delivery device having an improved ability to consistently and effectively deliver a drug formulation through a patient's skin.

BRIEF DESCRIPTION OF THE INVENTION

Aspects and advantages of the invention will be set forth in part in the following description, or may be obvious from the description, or may be learned through practice of the invention.

In one aspect, the present subject matter is directed to a transdermal drug delivery device. The device may comprise a housing including an upper housing portion and a lower housing portion. The lower housing portion may define a bottom surface including skin attachment means for releasably attaching the lower housing portion to skin of a user. The upper housing portion may at least partially surround a central region of the device. The device may also include a microneedle assembly and a reservoir disposed within the central region. The reservoir may be in fluid communication with the microneedle assembly. Additionally, the device may include a pushing element disposed above the microneedle assembly within the central region. The pushing element may be configured to provide a continuous bilateral force having a downward component transmitted through the microneedle assembly and an upward component transmitted through the skin attachment means.

In another aspect, the present subject matter is directed to a transdermal drug delivery device. The device may include an upper housing attached to a lower housing defining a cavity. The lower housing may define a bottom surface including skin attachment means for releasably attaching the lower housing to skin of a user. The lower housing may also define an opening and may surround a microneedle assembly. The device may be configured such that the lower housing is dissociated from the microneedle assembly. In addition, the device may include a reservoir disposed within the cavity that is in fluid communication with the microneedle assembly. Moreover, the device may include a pushing element disposed within the cavity between the microneedle assembly and the upper housing. The pushing element may be configured so as to be dissociated from the lower housing and may provide (i) a continuous force having a downward component, dissociated from the upper and lower housings, transmitted via the microneedle assembly towards the skin of a user, (ii) a continuous force having an upward component, dissociated from the microneedle assembly, transmitted to the lower housing.

In a further aspect, the present subject matter is directed to a method for transdermally delivering a drug formulation. The method may generally include positioning a transdermal drug delivery device adjacent to skin, attaching a housing of the device to the skin via a skin attachment means, applying, with a pushing element, a continuous bilateral force having a downward component transmitted through a microneedle assembly of the device and an upward component transmitted through the skin attachment means delivering the drug formulation from through the microneedle assembly and into or through the skin.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention directed to one of ordinary skill in the art, is set forth in the specification, which makes reference to the appended figures, in which.

DETAILED DESCRIPTION OF THE INVENTION

Figure 1:
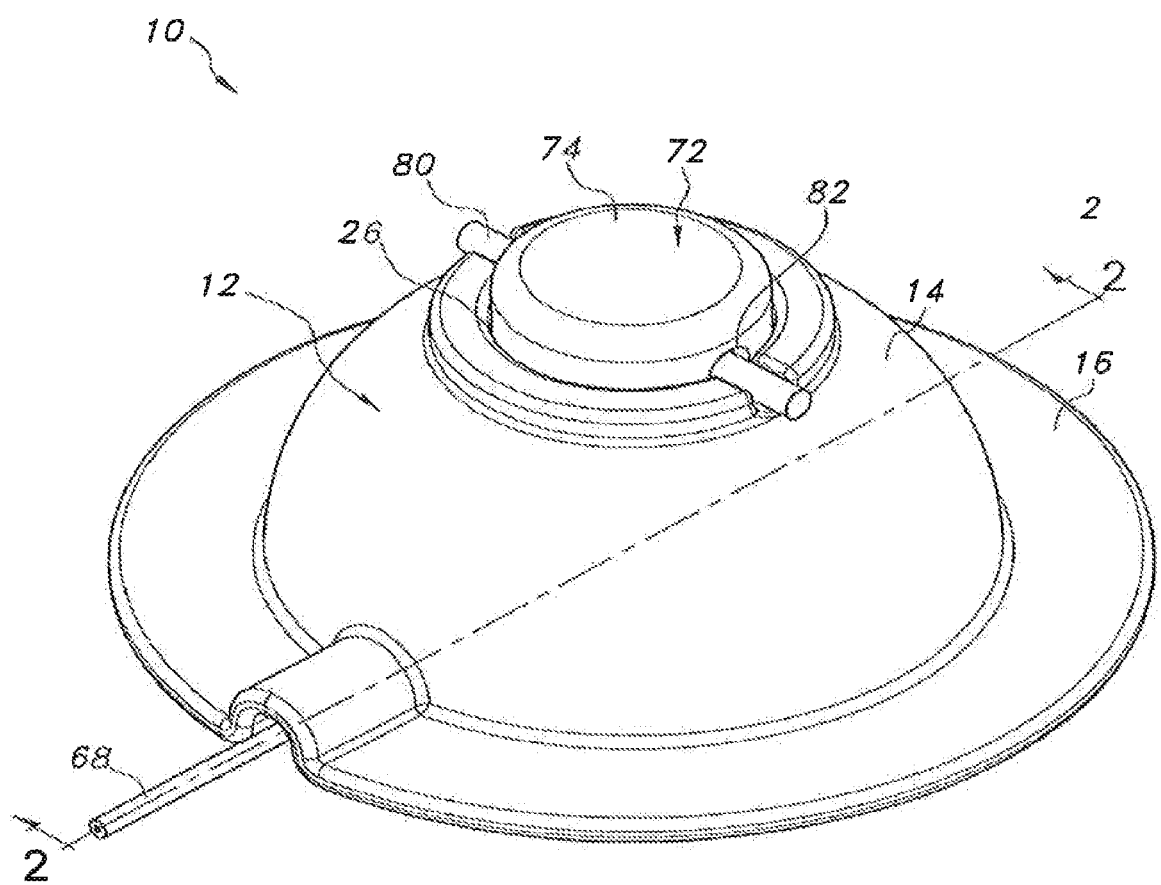
FIG. 1 illustrates an assembled, perspective view of one embodiment of a transdermal drug delivery device in accordance with aspects of the present subject matter.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to a transdermal drug delivery device configured to deliver a drug formulation into and/or through a user's skin. The device may generally include a housing configured to encase or surround various components of the device, with at least a portion of the housing being configured to be attached to the user's skin. The device may also include a reservoir in fluid communication with a microneedle assembly. The reservoir may generally be configured to retain a drug formulation for subsequent delivery through the user's skin via the microneedle assembly. In addition, the device may include a pushing element configured to apply a continuous bilateral force through the device. Specifically, in several embodiments, the pushing element may be configured to apply a continuous downward force through the microneedle assembly to push the microneedles of the assembly into the user's skin. Simultaneously, the pushing element may be configured to apply a continuous upward force against the housing that is transmitted through the housing to the user's skin (via a suitable skin attachment means disposed between the housing and the skin), thereby providing a tensioning force that tightens the user's skin around the microneedle assembly to enhance insertion and maintenance of the microneedles into/within the skin.

Referring now to the drawings, FIGS. 1-4 illustrate several views of one embodiment of a transdermal drug delivery device 10 in accordance with aspects of the present subject matter. As shown, the device 10 may include an outer housing 12 configured to at least partially surround and/or encase the various components of the device 10. In general, the housing 12 may include an upper housing portion 14 and a lower housing portion 16 formed integrally with and/or extending from the upper housing portion 14. The upper housing portion 14 may generally be configured to define an open volume for housing the various device components. For example, as shown FIGS. 2 and 3, when the device 10 is placed onto the user's skin 18, an open volume may be defined between the user's skin 18 and the upper housing portion 14 within which the device components may be contained. It should be appreciated that the upper housing portion 14 may generally be configured to define any suitable shape. For instance, as shown in the illustrated embodiment, the upper housing portion 14 defines a semi-circular or dome shape. However, in other embodiments, the upper housing portion 14 may have any other suitable shape that defines an open volume for housing the various components of the device 10.

The lower housing portion 16 of the housing 12 may generally be configured to be positioned adjacent to the user's skin when the device 10 is in use. For example, as shown in the illustrated embodiment, the lower housing portion 16 may be configured as a flange or projection extending outwardly from the bottom periphery of the upper housing portion 14 such that a bottom surface 20 of the lower housing portion 16 may extend directly adjacent to the user's skin 18. Additionally, in several embodiments, the lower housing portion 16 may be configured to be attached to the user's skin 18 using any suitable skin attachment means. For example, in one embodiment, an adhesive layer 22 may be applied to the bottom surface 20 of the lower housing portion 16. As such, when the device 10 is placed onto the user's skin 18, the housing 12 may be attached to the skin 18 via the adhesive layer 22. However, in other embodiments, any other suitable skin attachment means known in the art may be utilized to attach the housing 12 to the user's skin 18.

Figure 2:
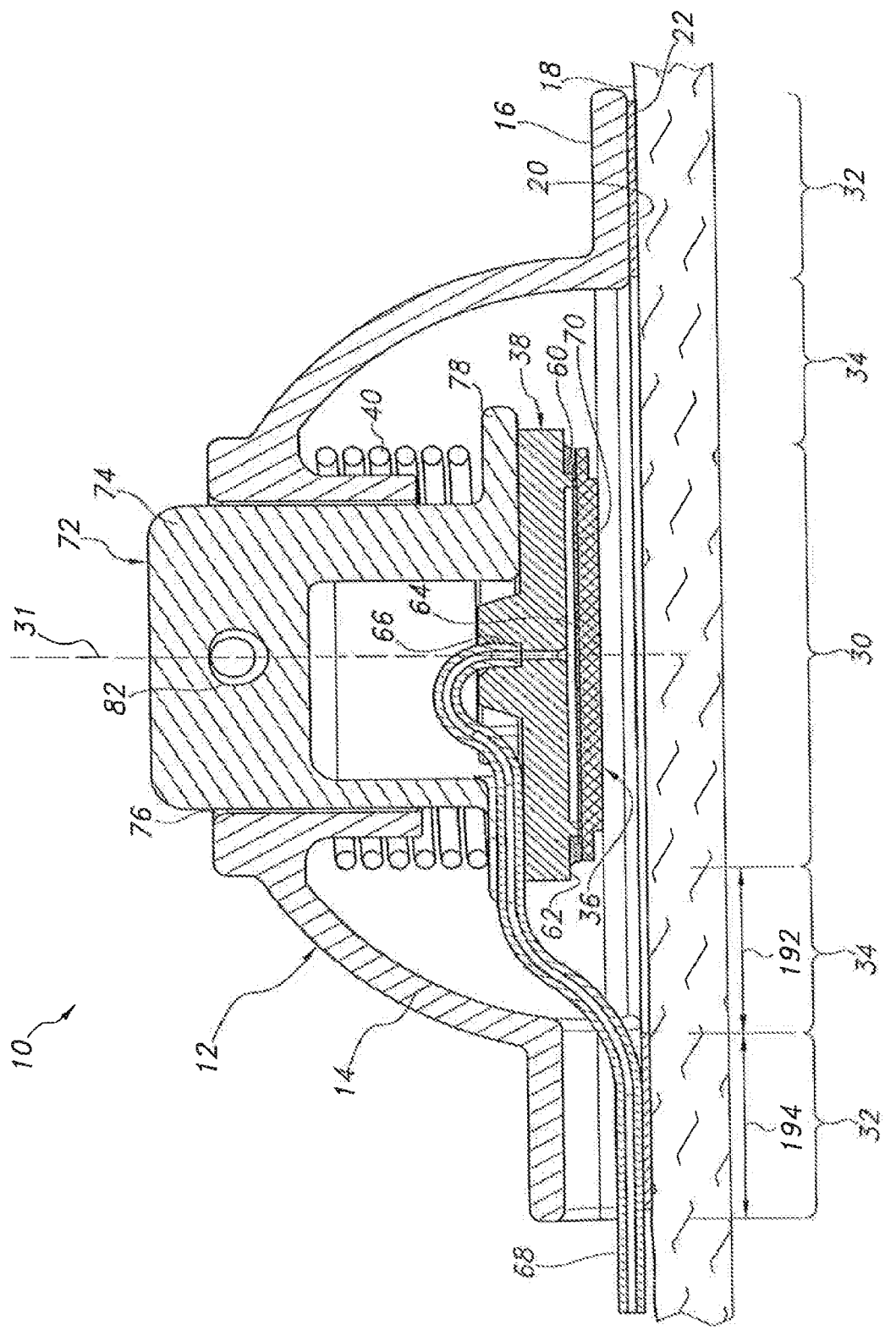
FIG. 2 illustrates a cross-sectional view of the device shown in FIG. 1 taken about line 2-2, particularly illustrating various components of the device in an un-actuated position.
Figure 3:
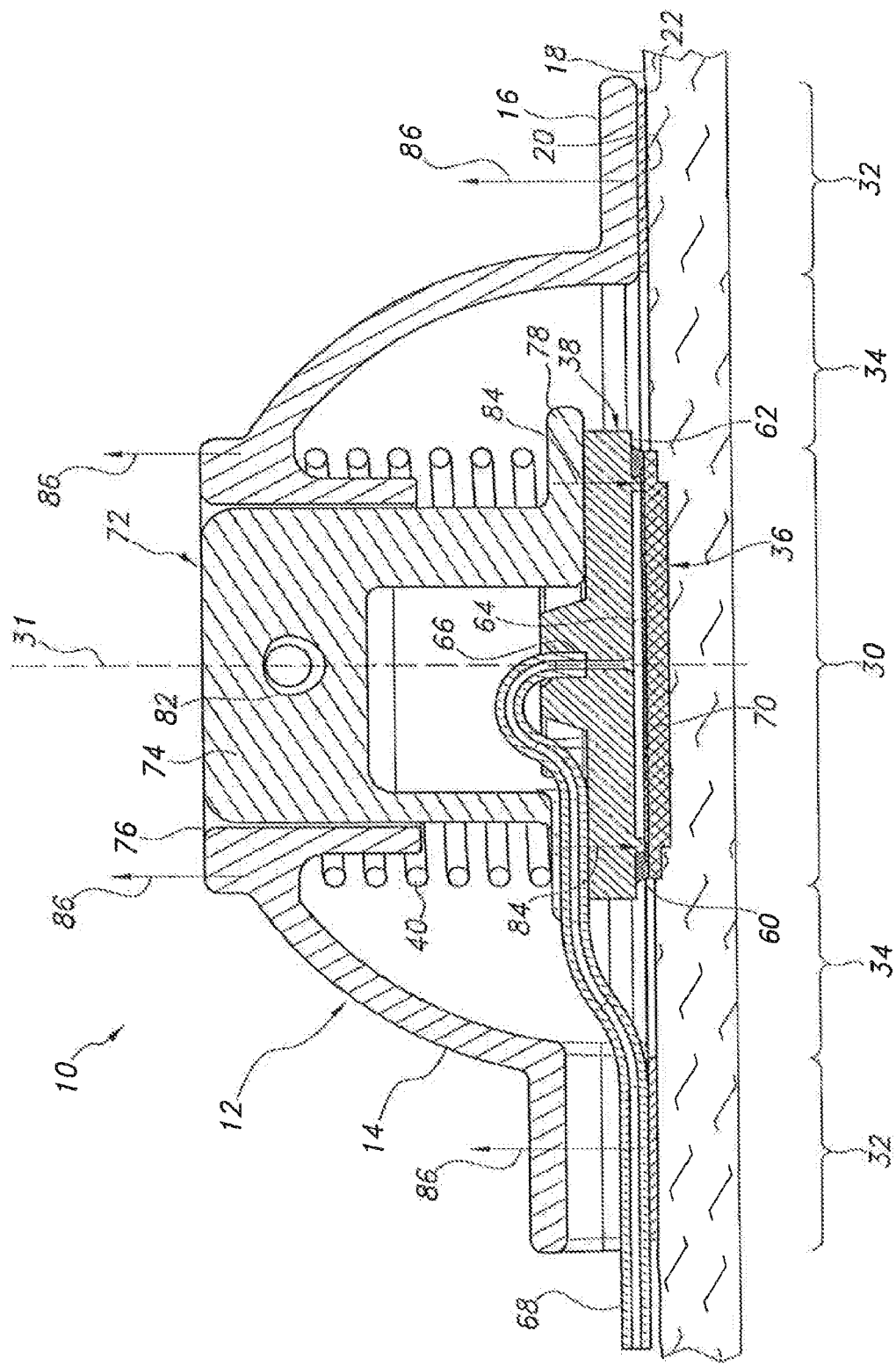
FIG. 3 illustrates another cross-sectional view of the device shown in FIG. 1 taken about line 2-2, particularly illustrating various components of the device in an actuated position.

Additionally, as particularly shown in FIGS. 2 and 3, different zones or regions of the device 10 may be defined by and/or within the housing 12. For example, the device 10 may include a central region 30 defined around its center line 31. The device 10 may also include an outer region 32 generally defined around the device periphery at the location at which the device 10 is attached to the user's skin 18. For example, as shown in FIGS. 2 and 3, the outer region 32 may be defined at the interface between the bottom surface 20 of the lower housing portion 16 and the adhesive layer 22 securing the housing 12 to the user's skin 18. Moreover, the device 10 may include an intermediate region 34 extending between and separating the central and outer regions 30, 32.

In several embodiments, the device 10 may include one or more components at least partially disposed within the central region 30. For example, as shown in the illustrated embodiment, the device 10 includes a microneedle assembly 36, a reservoir 38 and a bilateral pushing element 40 vertically aligned within the central region 30, with the footprint of such components generally defining the outer perimeter of the central region 30. As will be described below, the pushing element 40 may be configured to apply a downward force through the central region 30 in order to press the microneedle assembly 36 into the user's skin 18. In addition, the pushing element 40 may also be configured to apply an upward force through the central region 30 that is transmitted through the housing 12 to the outer region 32 of the device 10, thereby providing an upward force against the user's skin 18 via the adhesive layer 22.

Figure 11:
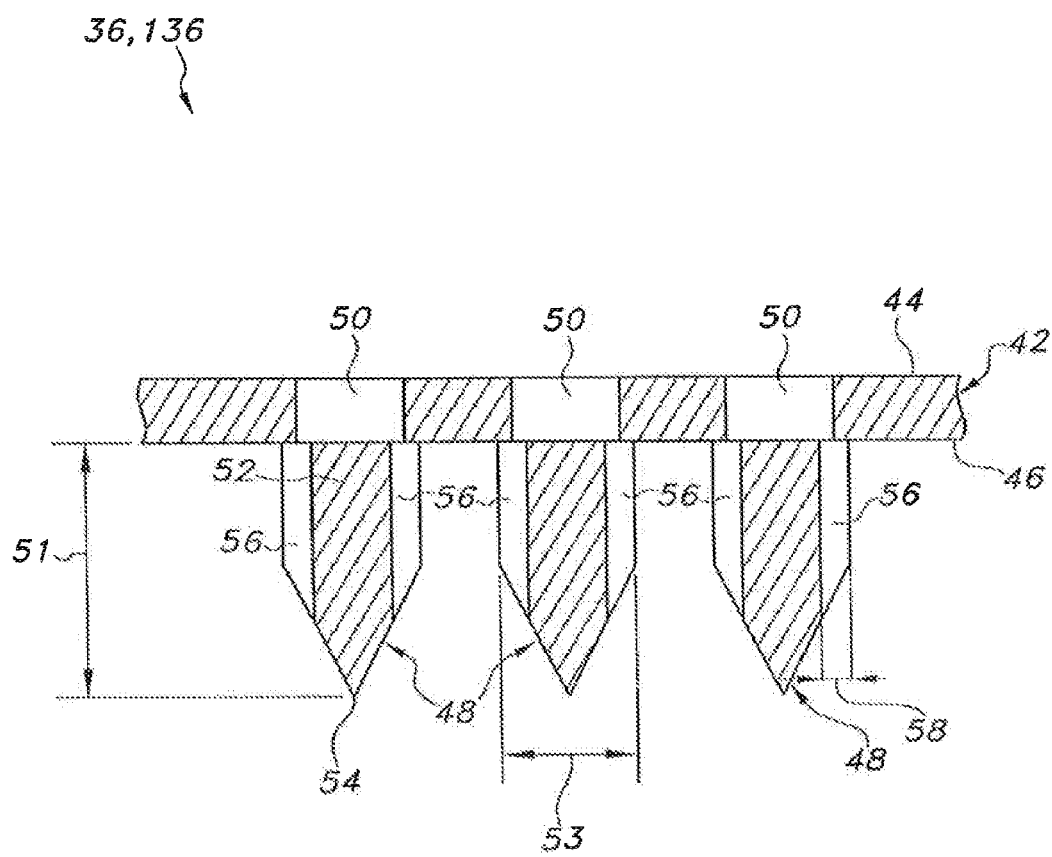
FIG. 11 illustrates a close-up, partial view of one embodiment of a microneedle assembly configuration suitable for use with the disclosed transdermal drug delivery devices.

In general, the microneedle assembly 36 of the device 10 may have any suitable configuration known in the art for delivering a fluidic drug formulation into and/or through the user's skin 18, such as by being configured to include a plurality of microneedles extending outwardly from a suitable substrate or support. For example, a partial, cross-sectional view of one embodiment of a suitable microneedle assembly configuration is illustrated in FIG. 11. As shown, the microneedle assembly 36 may include a support 42 defining a top surface 44 and a bottom surface 46 and a plurality of microneedles 48 extending outwardly from the bottom surface 46. The support 42 may generally be constructed from a rigid, semi-rigid or flexible sheet of material, such as a metal material, a ceramic material, a plastic material and/or any other suitable material. In addition, the support 42 may define one or more apertures between its top and bottom surfaces 44, 46 to permit the drug formulation to flow therebetween. For example, as shown in FIG. 11, a single aperture 50 may be defined in the support 42 at the location of each microneedle 48 to permit the drug formulation to be delivered from the top surface 44 to such microneedle 48. However, in other embodiments, the support 42 may define any other suitable number of apertures 50 positioned at and/or spaced apart from the location of each microneedle 48

Additionally, as shown in FIG. 11, each microneedle 48 of the microneedle assembly 36 may generally be configured to define a piercing or needle-like shape (e.g., a conical or pyramidal shape or a cylindrical shape transitioning to a conical or pyramidal shape) extending between a base 52 positioned adjacent to and/or extending from the bottom surface 46 of the support 42 and a tip 54 disposed opposite the base 52. As is generally understood, the tip 54 may correspond to the point of each microneedle 48 that is disposed furthest away from the support 42 and may define the smallest dimension of each microneedle 48. Additionally, each microneedle 48 may generally define any suitable length 51 between its base 52 and its tip 54 that is sufficient to allow the microneedles 48 to penetrate the stratum corneum and pass into the epidermis. In several embodiments, it may be desirable to limit the length 51 of the microneedles 48 such that they do not penetrate through the inner surface of the epidermis and into the dermis; such embodiments advantageously help minimize pain for the patient receiving the drug formulation. For example, in one embodiment, each microneedle 48 may define a length 51 of less than about 1000 micrometers (um), such as less than about 800 um, or less than about 750 um or less than about 500 um and any other subranges therebetween. In a particular embodiment, the length 51 may range from about 25 um to about 1000 um, such as from about 100 um to about 1000 um or from about 200 um to about 1000 um and any other subranges therebetween.

It should be appreciated that the length 51 of the microneedles 48 may vary depending on the location at which the disclosed device is being used on a user. For example, the length of the microneedles 48 for a device to be used on a user's leg may differ substantially from the length of the microneedles 48 for a device to be used on a user's arm.

Moreover, each microneedle 48 may generally define any suitable aspect ratio (i.e., the length 51 over a cross-sectional dimension 53 of each microneedle 48). However, in certain embodiments, the aspect ratio may be greater than 2, such as greater than 3 or greater than 4. It should be appreciated that, in instances in which the cross-sectional dimension 53 (e.g., width, diameter, etc.) varies over the length of each microneedle 26 (e.g., as shown in FIG. 11), the aspect ratio may be determined based on the average cross-sectional dimension 53.

Further, each microneedle 48 may define one or more channels 56 in fluid communication with the apertures 50 defined in the support 42. In general, the channels 56 may be defined at any suitable location on and/or within each microneedle 48. For example, as shown in FIG. 11, in one embodiment, the channels 56 may be defined along an exterior surface of each microneedle 48. In another embodiment, the channels 56 may be defined through the interior of the microneedles 48 such that each microneedle 48 forms a hollow shaft. Regardless, the channels 56 may generally be configured to form a pathway that enables the drug formulation to flow from the top surface 44 of the support 42, through the apertures 50 and into the channels 56, at which point the drug formulation may be delivered into and/or through the user's skin 18.

It should be appreciated that the channels 56 may be configured to define any suitable cross-sectional shape. For example, in one embodiment, each channel 56 may define a semi-circular or circular shape. In another embodiment, each channel 56 may define a non-circular shape, such as a "v" shape or any other suitable cross-sectional shape.

In several embodiments, the dimensions of the channels 56 defined by the microneedles 48 may be specifically selected to induce a capillary flow of the drug formulation. As is generally understood, capillary flow occurs when the adhesive forces of a fluid to the walls of a channel are greater than the cohesive forces between the liquid molecules. Specifically, the capillary pressure within a channel is inversely proportional to the cross-sectional dimension of the channel and directly proportional to the surface energy of the subject fluid, multiplied by the cosine of the contact angle of the fluid at the interface defined between the fluid and the channel. Thus, to facilitate capillary flow of the drug formulation through the microneedle assembly 36, the cross-sectional dimension 58 (FIG. 11) of the channel(s) 56 (e.g., the diameter, width, etc.) may be selectively controlled, with smaller dimensions generally resulting in higher capillary pressures. For example, in several embodiments, the cross-sectional dimension 58 may be selected so that the cross-sectional area of each channel 56 ranges from about 1,000 square microns (um.sup.2) to about 125,000 um.sup.2, such as from about 1,250 um.sup.2 to about 60,000 um.sup.2 or from about 6,000 um.sup.2 to about 20,000 um.sup.2 and any other subranges therebetween.

It should be appreciated that FIG. 11 only illustrates a portion of a suitable microneedle assembly configuration and, thus, the microneedle assembly 36 used within the device 10 may generally include any number of microneedles 48 extending from its support 42. For example, in one embodiment, the actual number of microneedles 48 included within the microneedle assembly 36 may range from about 10 microneedles per square centimeter (cm.sup.2) to about 1,500 microneedles per cm.sup.2, such as from about 50 microneedles per cm.sup.2, to about 1250 microneedles per cm.sup.2 or from about 100 microneedles per cm.sup.2 to about 500 microneedles per cm.sup.2 and any other subranges therebetween.

It should also be appreciated that the microneedles 48 may generally be arranged on the support 42 in a variety of different patterns, and such patterns may be designed for any particular use. For example, in one embodiment, the microneedles 48 may be spaced apart in a uniform manner, such as in a rectangular or square grid or in concentric circles. In such an embodiment, the spacing of the microneedles 48 may generally depend on numerous factors, including, but not limited to, the length and width of the microneedles 48, as well as the amount and type of drug formulation that is intended to be delivered through the microneedles 48. By way of non-limiting example, microneedle arrays suitable for use with the present invention include those described in WO2012/020332 to Ross; WO2001/0270221 to Ross; and WO2011/070457 to Ross.

Referring back to FIGS. 1-4, as indicated above, the disclosed device 10 may also include a reservoir 38 in fluid communication with the microneedle assembly 36. Specifically, as shown in FIGS. 2 and 3, the reservoir 38 may be positioned above the microneedle assembly 36 within the central region 30 of the device 10. In several embodiments, the reservoir 38 may be configured to be attached to a portion of the microneedle assembly 36. For example, as shown in FIGS. 2 and 3, an adhesive layer 60 may be disposed between a bottom surface 62 of the reservoir 38 and the top surface of the microneedle assembly 36 (i.e., the top surface 44 of the support 42) in order to secure the microneedle assembly 36 to the reservoir 38.

In general, the reservoir 38 may have any suitable structure and/or may be formed from any suitable material that permits the reservoir 38 to initially retain the drug formulation prior to its subsequent delivery into the microneedle assembly 36. Thus, it should be appreciated that, as used herein, the term "reservoir" may generally refer to any suitable designated area or chamber within the device 10 that is configured to retain a fluidic drug formulation. For example, as shown in the illustrated embodiment, the reservoir 38 may be configured as a rigid or semi-rigid member defining an open volume or cavity 64 for retaining the drug formulation. However, in other embodiments, the reservoir 38 may have any other suitable configuration. For example, in another embodiment, the reservoir 38 may be configured as a flexible bladder. In a further embodiment, the reservoir 38 may be configured as a solid container or matrix through which the drug formulation is capable of being directed, such as a permeable, semi-permeable or microporous solid matrix. In still a further embodiment, the reservoir 38 may comprise a flexible bladder contained within or shielded by a rigid member.

It should be appreciated that any suitable drug formulation(s) may be retained within reservoir 38 and subsequently delivered through the user's skin 18 via the microneedle assembly 36. As used herein, the term "drug formulation" is used in its broadest sense and may include, but is not limited to, any drug (e.g., a drug in neat form) and/or any solution, emulsion, suspension and/or the like containing a drug(s). Similarly, the term "drug" is used in its broadest sense and includes any compound having or perceived to have a medicinal benefit, which may include both regulated and unregulated compounds. For example, suitable types of drugs may include, but are not limited to, biologics, small molecule agents, vaccines, proteinaceous compounds, anti-infection agents, hormones, compounds regulating cardiac action or blood flow, pain control agents and so forth. One of ordinary skill in the art should readily appreciate that various ingredients may be combined together in any suitable manner so as to produce a compound having or perceived to have a medicinal benefit.

It should also be appreciated that the drug formulation may be supplied to the reservoir 38 in a variety of different ways. For example, in several embodiments, the drug formulation may be supplied via an inlet channel 66 defined through a portion of the reservoir 38. In such an embodiment, a suitable conduit, port or tube 68 (e.g., a micro-bore tube or any other suitable flexible tube) may be configured to be received within the inlet channel 66 and may be in fluid communication with a suitable drug source (e.g., a syringe containing the drug formulation) such that the drug formulation may be directed through the inlet channel 66 and into the reservoir 38. In other embodiments, the drug formulation may be supplied to the reservoir 38 using any other suitable means/method. For example, the reservoir 38 may be configured to be pre-filled or pre-charged prior to being assembled into the device 10.

Figure 4:
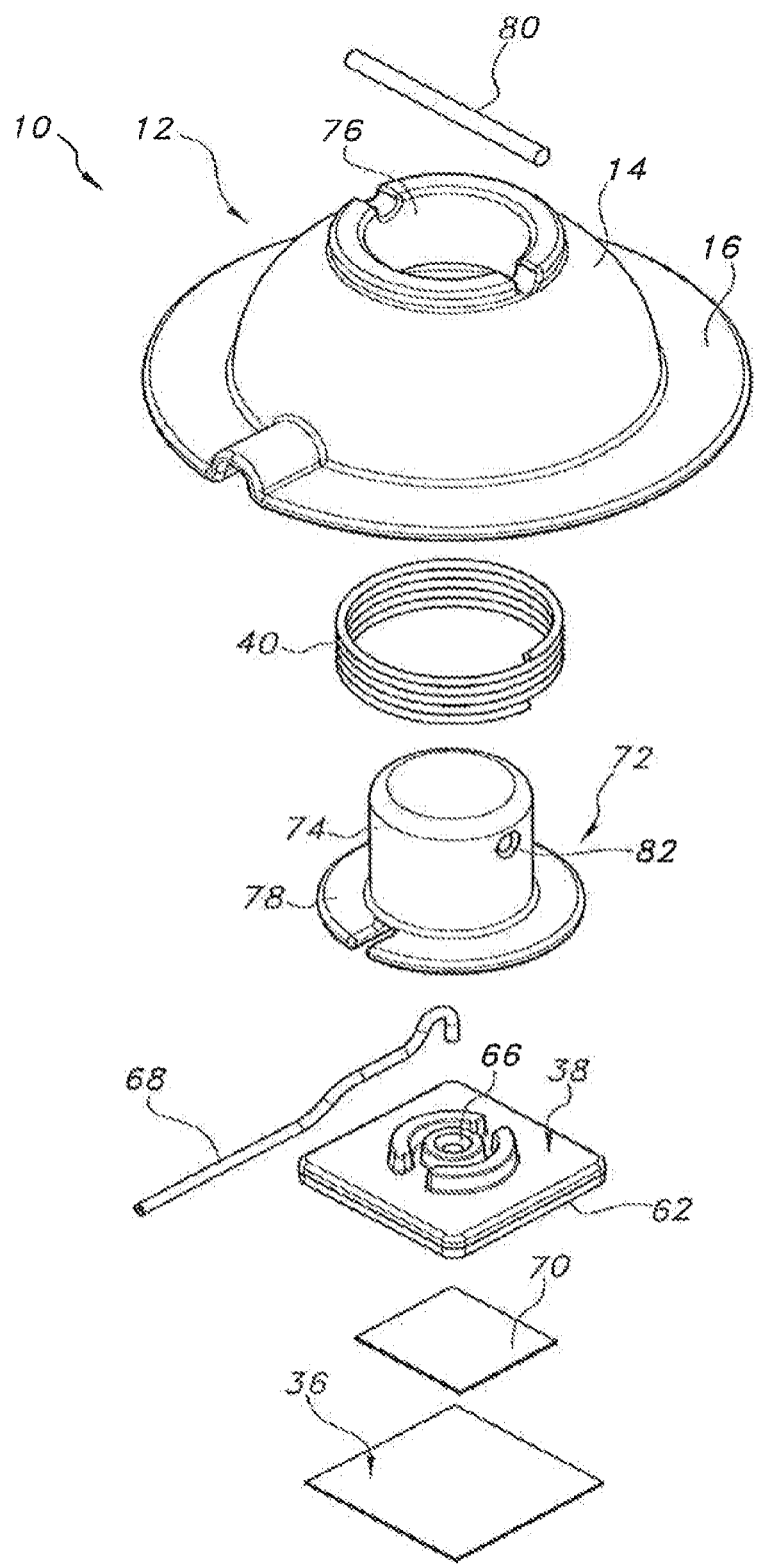
FIG. 4 illustrates an exploded, perspective view of the device shown in FIGS. 1-3.

Additionally, as particularly shown in FIG. 4, the device 10 may also include a rate control membrane 70 disposed between the reservoir 38 and the microneedle assembly 36. In general, the rate control membrane 70 may be configured to slow down or otherwise control the flow rate of the drug formulation as it is released from the reservoir 38. The particular materials, thickness, etc. of the rate control membrane 70 may, of course, vary based on multiple factors, such as the viscosity of the drug formulation, the desired delivery time, etc.

In several embodiments, the rate control membrane 70 may be fabricated from any suitable permeable, semi-permeable or microporous material(s). For example, in several embodiments, the material used to form the rate control membrane 70 may have an average pore size of from about 0.01 micron to about 1000 microns, such as from about 1 micron to about 500 microns or from about 20 microns to about 200 microns and any other subranges therebetween. Additionally, in a particular embodiment, the material used to form the rate control membrane 70 may have an average pore size ranging from about 0.01 micron to about 1 micron, such as from about 0.1 micron to about 0.9 micron or from about 0.25 micron to about 0.75 micron and any other subranges therebetween, Suitable membrane materials include, for instance, fibrous webs (e.g., woven or nonwoven), apertured films, foams, sponges, etc., which are formed from polymers such as polyethylene, polypropylene, polyvinyl acetate, ethylene n-butyl acetate and ethylene vinyl acetate copolymers.

Referring still to FIGS. 1-4, the device 10 may also include a plunger 72 positioned directly above of the reservoir 38. In general, the plunger 72 may be configured to be moved relative to the housing 12 as the various components contained within the housing 12 are moved between un-actuated position (FIG. 2), wherein the bottom of the microneedle assembly 36 is generally aligned with or recessed relative to the bottom surface 20 of the lower housing portion 16 and an actuated position (FIG. 3), wherein the microneedle assembly 36 extends outward beyond the bottom surface 20 of the lower housing portion 16, thereby allowing the microneedles 48 of the assembly 36 to penetrate the user's skin 18. As shown in FIGS. 2-4, in one embodiment, the plunger 72 may generally include a cylindrical top portion 74 configured to be slidably received within a corresponding opening 76 defined in the housing 12 and a flattened bottom portion 78 configured to engage or otherwise be positioned directly adjacent to the reservoir 38. In such an embodiment, when the plunger 72 is moved downward relative to the housing 12, the bottom portion 78 of the plunger 72 may apply a force against the reservoir 38 that pushes the microneedle assembly 36 downward into the user's skin 18.

Additionally, as indicated above, the disclosed device 10 may also include a bilateral pushing element 40 disposed within the central region 30 of the device 10. In general, the pushing element 40 may be any suitable biasing mechanism and/or force application means that is configured to apply a continuous bilateral force (having both a downward component and an upward component) through the device 10 to the user's skin 18. For example, as shown in the illustrated embodiment, the pushing element 40 comprises a spring compressed between the housing 12 and the plunger 72. Thus, when the device 10 is moved to the actuated position during use (FIG. 3), the spring may be configured to apply a continuous bilateral force against the housing 12 and the plunger 72 that is transmitted through the device 10 to the user's skin 18. Specifically, the downward component of the force (indicated by arrows 84 in FIG. 3) may be transmitted downward through the central region 30 of the device 10 (i.e., through the plunger 72 and the reservoir 38) to the microneedle assembly 36 such that the microneedles 48 of the assembly 36 are pressed into and maintained within the user's skin 18. Similarly, the upward component of the force (indicated by arrows 86 in FIG. 3) may be transmitted upward through the central region 30 of the device 10 to the housing 12, thereby pushing housing 12 away from the user's skin 18. However, since the housing 12 is attached to the user's skin 18 around its outer periphery (i.e., at the outer region 32 of the device 10), such upward force may generally be transmitted through the housing 12 and the adhesive layer 22 so as to provide an upward, tensioning force against the user's skin 18. Thus, as the microneedles 48 are pushed downward into the user's skin 18, the user's skin 18 may simultaneously be pulled upwards around the periphery of the device 10, thereby tightening the skin 18 around the microneedle assembly 36 and enhancing the ease at which the microneedles 48 may be inserted into and maintained within the user's skin 18.

In several embodiments, the device 10 may also include a locking mechanism configured to maintain the device components in the un-actuated position when the device 10 is not use. For example, as shown in FIG. 1, a lock pin 80 may be configured to extend through an opening 82 defined in the plunger 72 so as to engage opposing sides of the upper housing portion 14, thereby maintaining the spring in a compressed or un-actuated state. However, when the lock pin 80 is removed, the spring may be decompressed so that the continuous bilateral force is transmitted through the device 10 to the user's skin 18. In alternative embodiments, the locking mechanism may have any other suitable configuration and/or may be associated with any other suitable component of the device 10.

It should be appreciated that, as an alternative to the spring/lock pin 80 arrangement, the plunger 72 may be moved between the un-actuated and actuated positions using any other suitable arrangement and/or configuration known in the art.

For example, in another embodiment, the top portion 74 of the plunger 72 extending outwardly beyond the top of the upper housing portion 14 may be used as a push-button to manually push the plunger 72 downward into the actuated position. In such an embodiment, the bottom of the spring 40 may, for example, be coupled to the plunger 72 so that the spring 40 biases the plunger 72 into the un-actuated position.

It should be noted that, since the reservoir 38 may be configured as a rigid or semi-rigid member in the illustrated embodiment, the force applied by the pushing element 40 is transmitted through the body of the reservoir 38 instead of being transmitted to the drug formulation itself. Accordingly, the microneedles 48 may be pressed into the user's skin 18 without increasing the pressure of the drug formulation or otherwise applying a significant downward force upon the drug formulation. Stated differently, the pushing element 40, when actuated and applying a downward force on the microneedle assembly 36, does not pressurize the fluidized drug passing out of the device and into the skin through the microneedle channels 56.

Figure 5:
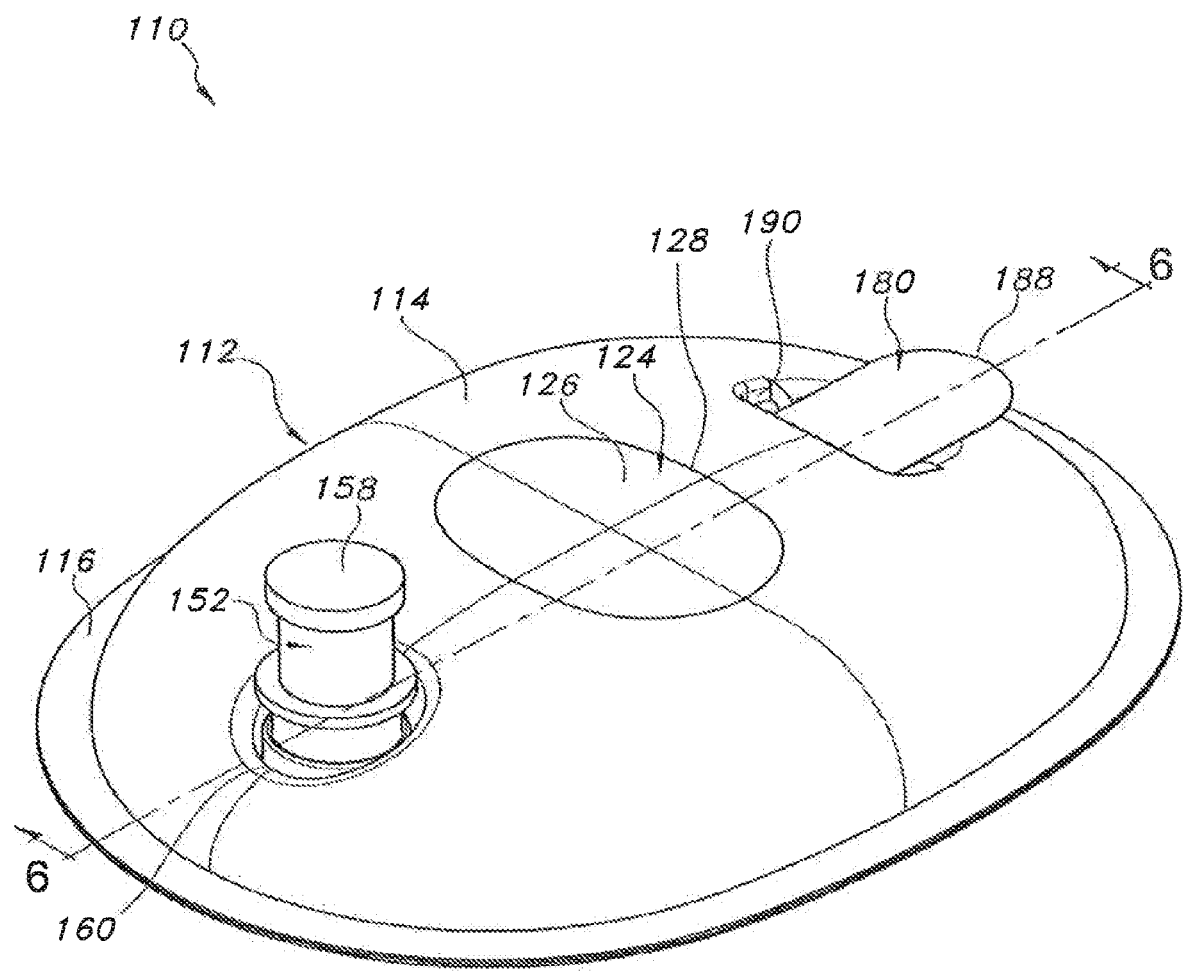
FIG. 5 illustrates an assembled, perspective view of another embodiment of a transdermal drug delivery device in accordance with aspects of the present subject matter.
Figure 6:
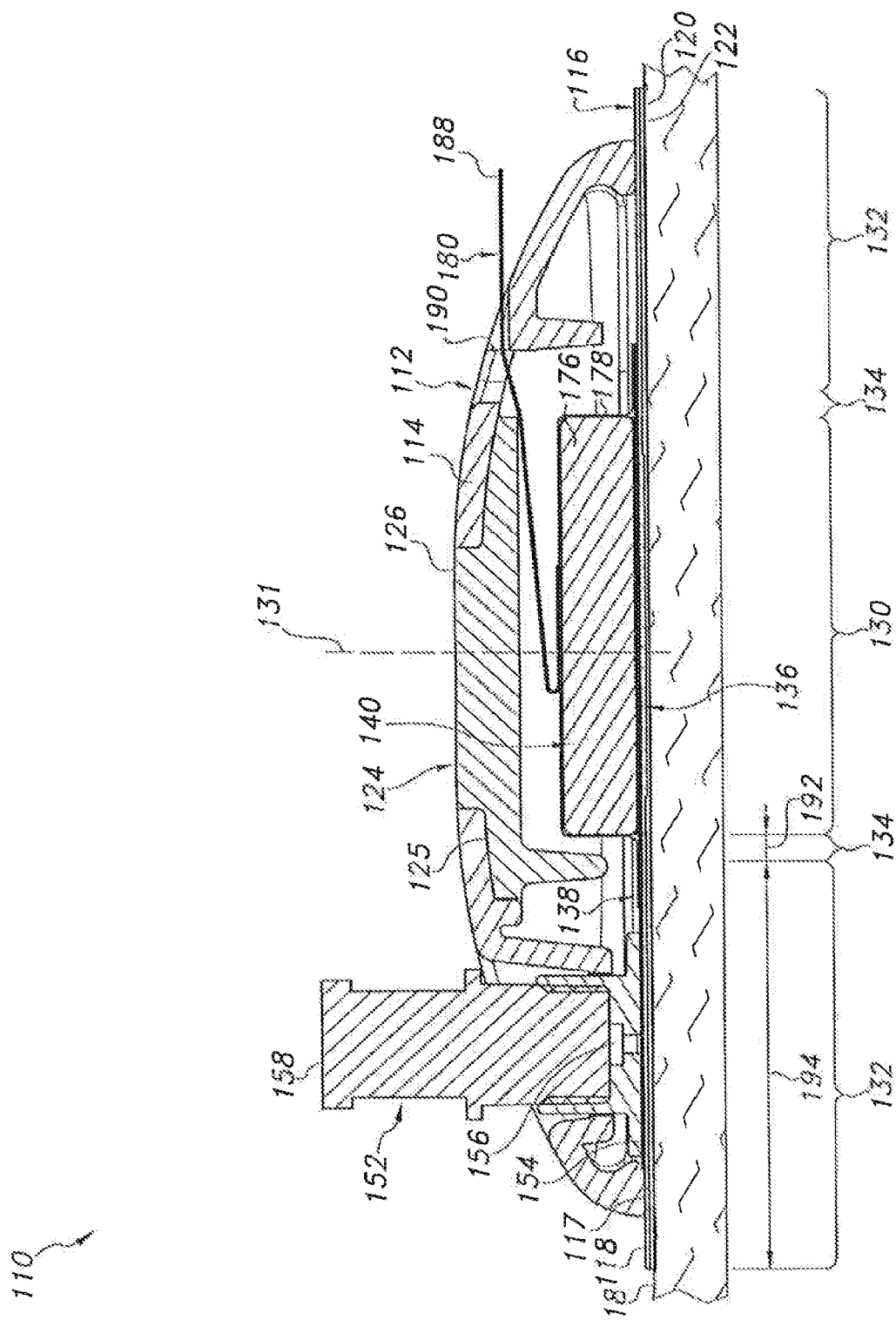
FIG. 6 illustrates a cross-sectional view of the device shown in FIG. 5 taken about line 6-6, particularly illustrating various components of the device in an un-actuated position.
Figure 7:
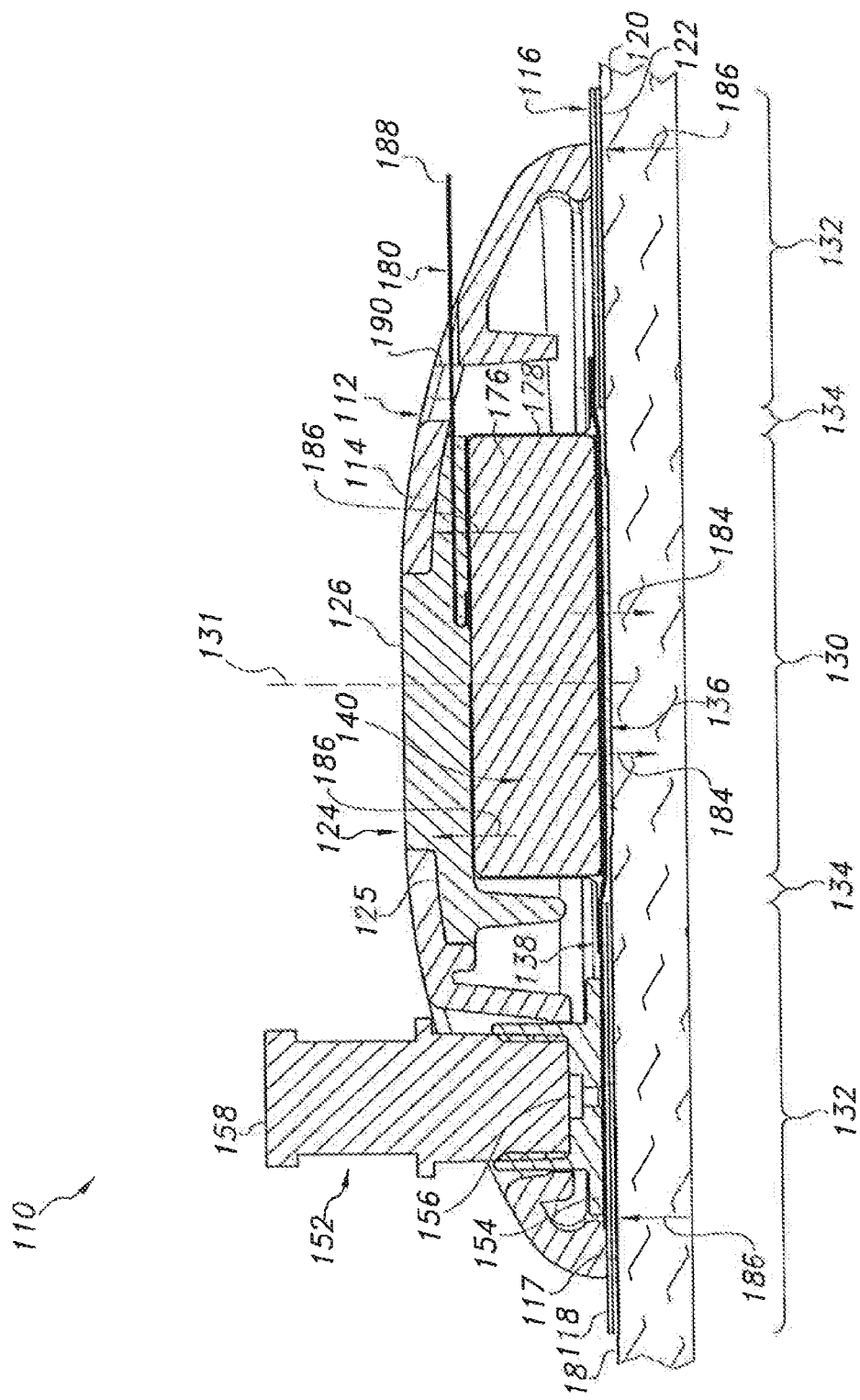
FIG. 7 illustrates another cross-sectional view of the device shown in FIG. 6, particularly illustrating various components of the device in an actuated position.
Figure 8:
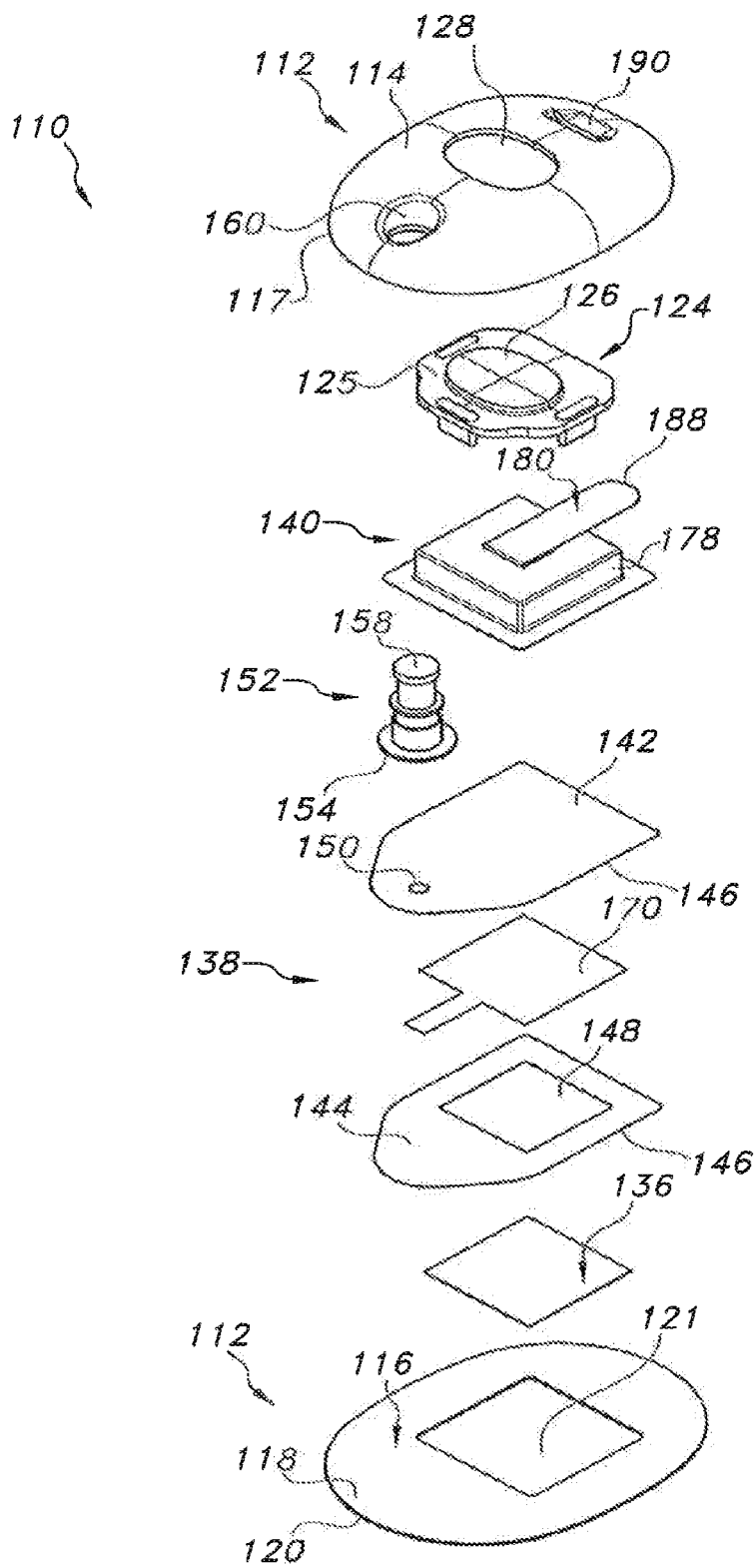
FIG. 8 illustrates an exploded, perspective view of the device shown in FIGS. 5-7.

Referring now to FIGS. 5-10, several views of another embodiment of a transdermal drug delivery device 110 are illustrated in accordance with aspects of the present subject matter. As shown, the device 110 may include an outer housing 112 configured to at least partially surround and/or encase the various components of the device 110. In general, the housing 112 may include an upper housing portion 114 and a lower housing portion 116. However, unlike the housing 12 described above with reference to FIGS. 1-4, the upper housing portion 114 and the lower housing portion 116 may comprise separate components configured to be separately attached to one another. For example, as shown in FIGS. 6-8, in one embodiment, a bottom peripheral surface 117 of the upper housing portion 114 may be configured to be secured to a top surface 118 of the lower housing portion 116 using an adhesive, thermal bonding/welding or any other suitable attachment means.

In general, the upper housing portion 114 may be configured as an outer shell defining an open volume for housing the various device components. For example, as shown FIGS. 6 and 7, when the housing 112 is assembled, an open volume may be defined between the upper housing portion 114 and the lower housing portion 116 within which the device components may be at least partially contained. It should be appreciated that the upper housing portion 114 may be configured to define any suitable shape. For instance, as shown in the illustrated embodiment, the upper housing portion 114 generally defines a semicircular or dome shape. However, in other embodiments, the upper housing portion 114 may have any other suitable shape that defines an open volume for housing the various components of the device 10. The lower housing portion 116 of the housing 112 may generally be configured to be positioned adjacent to the user's skin 18 when the device 110 is in use. For example, as shown in the illustrated embodiment, the lower housing portion 116 may comprise a flat panel configured to extend both inwardly and outwardly from the bottom peripheral surface 117 of the upper housing portion 114 such that a bottom surface 120 of the lower housing portion 116 extends directly adjacent to the user's skin 18. Additionally, as shown in FIG. 8, the lower housing portion 116 may define a central opening 121 through which the user's skin 18 may be accessed. For instance, as will be described below, a microneedle assembly 136 of the device 110 may be configured to extend through the opening 121 to allow such assembly to penetrate the user's skin 18.

Moreover, in several embodiments, the lower housing portion 116 may be configured to be attached to the user's skin 18 using a suitable skin attachment means. For example, in one embodiment, an adhesive 122 may be applied to the bottom surface 120 of the lower housing portion 116. As such, when the device 10 is placed onto the user's skin 18, the housing 112 may be attached to the skin 18 via the adhesive layer 122. However, in other embodiments, any other suitable skin attachment means known in the art may be utilized to attach the housing 112 to the user's skin 18.

It should be appreciated that, in several embodiments, both the upper housing portion 114 and the lower housing portion 116 may be formed from a relatively flexible material, such as a flexible polymer material, to allow the housing 112 to generally conform the shape of the user's body and/or to facilitate proper adhesion to the skin 18. In such embodiments, the device 110 may also include a rigid support member 124 extending between the upper and lower housing portions 114, 116 so as to provide structural support to the device 110. For example, as shown in FIG. 8, the support member 124 may define a relatively flat platform 125. The flat underside of the platform 125 may, in one aspect, provide a flat or substantially flat surface relative to the bilateral pushing element such that the bilateral pushing element can achieve a reliable and/or even engagement with this surface when actuated. In addition, the support member 124 may further include an outward projection 126 extending upward from the platform 125. Additionally, as shown in FIG. 8, the upper housing portion 114 may be configured to define a support opening 128 configured to receive the projection 126. Thus, when the projection 126 is received within the support opening 128, at least a portion of the upper housing portion 114 may contact against and be supported by the platform 125. Moreover, the top of the support member 124 may also provide a load-bearing surface through which a force may be applied by the user when attaching the device 110 to the user's skin 18.

Similar to the embodiment described above with reference to FIGS. 1-4, the device 110 may include different zones or regions defined by and/or within the housing 112. For example, as shown in FIGS. 6 and 7, the device 110 may include a central region 130 defined around its center line 131. The device 110 may also include an outer region 132 generally defined at the location at which the device 110 is attached to the user's skin 18. For example, as shown in FIGS. 6 and 7, the outer region 132 may be defined at the interface between the bottom surface 120 of the lower housing portion 116 and the adhesive layer 122. Moreover, the device 110 may also include an intermediate region 134 extending between and separating the central and outer regions 130, 132.

In several embodiments, the device 110 may include one or more components at least partially disposed within the central region 130. For example, as shown in the illustrated embodiment, the device 110 may include a microneedle assembly 136, a reservoir 138 and a bilateral pushing element 140 vertically aligned within the central region 130, with the footprint of the microneedle assembly 136 and the pushing element 140 generally defining the outer perimeter of the central region 130. As will be described below, the pushing element 140 may be configured to apply a downward force through the central region 130 in order to press the microneedle assembly 136 into the user's skin 18. In addition, the pushing element 140 may also be configured to apply an upward force through the central region 130 that is transmitted through the housing 112 to the outer region 132 of the device 110, thereby providing an upward force against the user's skin 18 via the adhesive layer 122.

In general, the microneedle assembly 136 may be configured the same as or similar to the microneedle assembly 36 described above. For example, as shown in FIG. 11, in several embodiments, the microneedle assembly 136 may include a support 42 having a top surface 44 and a bottom surface 46 and defining a plurality of apertures 50 between the top and bottom surfaces 44, 46. In addition, the microneedle assembly 136 may also include a plurality of microneedles 48 extending outwardly from the bottom surface 46. As described above, each microneedle 48 may define a channel(s) 56 in fluid communication with the apertures 50. As such, the drug formulation contained within the device 110 may be directed from the top surface 44 of the support 42 through the apertures 50 and into the microneedles 48 for subsequent delivery to the user's skin 18.

Additionally, similar to the embodiment described above, the reservoir 138 of the device 110 may generally be configured as any suitable designated area or chamber within which the drug formulation may be initially retained prior to the subsequent delivery of the formulation to the microneedle assembly 136. For example, as shown in the illustrated embodiment, the reservoir 138 may be configured as a flexible bladder. Specifically, as shown in FIG. 8, the reservoir 138 may include a flexible top layer 142 and a flexible bottom layer 144, with the top and bottom layers 142, 144 being configured to be secured to one another around their edges 146. In such an embodiment, to allow the drug formulation retained within the reservoir 138 to be delivered to the microneedle assembly 136, the bottom layer 144 of the reservoir 138 may define an opening or window 148 that is in fluid communication with the microneedle assembly 136. For example, as shown FIG. 8, the window 148 may be defined in the bottom layer 144 such that, when the reservoir 138 is positioned directly above microneedle assembly 136, the drug formulation may be directed through the window 148 and along the top surface of the microneedle assembly 136 (i.e., the top surface 44 of the support 42).

It should be appreciated that the drug formulation may be supplied to the reservoir 138 in a variety of different ways. For example, in several embodiments, the drug formulation may be supplied via an inlet opening 150 defined in the top layer 142 (or the bottom layer 144) of the reservoir 138. In such an embodiment, a suitable conduit, port and/or tube may be in fluid communication within both the inlet opening 150 and a suitable drug source (e.g., a syringe containing the drug formulation) such that the drug formulation may be directed through the inlet opening 150 and into the reservoir 138. For example, as shown in FIGS. 6-8, a supply port 152 may include a bottom end 154 configured to be secured/sealed to the reservoir 138 around the inlet opening 150 such that the drug formulation may be delivered to the inlet opening 150 via a supply channel 156 defined through the bottom end 154. Additionally, as shown in FIG. 5, a top end 158 of the supply port 152 may be configured to extend through a port opening 160 defined in the upper housing portion 114. As such, the top end 158 may be accessed by the user or a healthcare professional to permit the drug formulation to be injected into the supply port 152. Although not shown, the supply port 152 may also be configured to include a one-way valve to allow the drug formulation to flow through the port 152 in the direction of the reservoir 138 (i.e., from the top end 158 to the bottom end 154) and to prevent the flow of such drug formulation in the opposite direction (i.e., from the bottom end 154 to the top end 158).

In other embodiments, the drug formulation may be supplied to the reservoir 138 using any other suitable means/method. For example, in one embodiment, the reservoir 138 may be configured to be pre-filled or pre-charged prior to being assembled into the device 10.

Additionally, the disclosed device 110 may also include a rate control membrane 170 to slow down or otherwise control the flow rate of the drug formulation as it is released into the microneedle assembly 136. Specifically, as shown in FIG. 8, the rate control membrane 170 may be configured to be secured within the reservoir 138 around the perimeter of the reservoir window 148 such that the drug formulation passes through the rate control membrane 170 prior to exiting the reservoir 138 via the window 148. However, in other embodiments, the rate control membrane 170 may be positioned between the bottom layer 144 of the reservoir 138 and the microneedle assembly 136 at the location of the window 148. It should be appreciated that the rate control membrane 170 may generally be configured the same as or similar to the rate control membrane 70 described above, such as by being fabricated from any suitable permeable, semi-permeable or microporous material(s) that allows for the membrane 170 to control the flow rate of the drug formulation flowing between the reservoir 138 and the microneedle assembly 136.

Referring still to FIGS. 5-10, as indicated above, the device 110 may also include a bilateral pushing element 140 disposed within the central region 130 of the device 110. In general, the pushing element 140 may comprise any suitable biasing mechanism and/or force application means that is configured to apply a continuous bilateral force (having both a downward component and an upward component) through the device 110 and against the user's skin 18. For example, as shown in the illustrated embodiment, the pushing element 140 comprises an expandable member positioned between the upper housing portion 114 and the reservoir 138. The expandable member may generally be configured to be in an un-expanded state (FIGS. 6 and 9), in which the member does not transmit any forces through the central region 130 of the device 100, and an expanded or actuated state (FIGS. 7 and 10), in which the member expands outwardly so as to apply a continuous bilateral force through the central region 130. For example, as particularly shown in FIGS. 9 and 10, the expandable member may be configured to define a first height 172 when in the un-expanded state and a larger, second height 174 when in the actuated state.

Such expansion may generally provide a means for the expandable member to apply both a continuous downward force and a continuous upward force through the central region 130 of the device 110. Specifically the downward component of the force (indicated by the arrows 184 in FIG. 7) may be transmitted downward through the central region 130 (e.g., through the reservoir 138) to the microneedle assembly 136 such that the microneedles 48 of the assembly 136 extend through the central opening 121 (FIG. 8) and are pressed into and maintained within the user's skin 18. It will be appreciated that, in such an embodiment, fluid within the reservoir 138 will be pressurized as a result of the downward pressure component exerted by the bilateral pushing element 140. Similarly, the upward component of the force (indicated by the arrows 186 in FIG. 7) may be transmitted upward through the central region 130 (e.g., through the support member 124) to the housing 112, thereby pushing the housing 112 away from the user's skin. However, since the housing 112 is attached to the user's skin 18 around its outer periphery (i.e., at the outer region 132 of the device 110), such upward force may generally be transmitted through the housing 112 to the adhesive layer 122 so as to provide an upward, tensioning force against the user's skin 18. Thus, as the microneedles 48 are pushed downward into the user's skin 18, the user's skin 18 may be pulled upwards around the device's periphery, thereby tightening the skin 18 around the microneedle assembly 36 and enhancing the ease at which the microneedles 48 may be inserted into and maintained within the user's skin 18.

Figure 9:
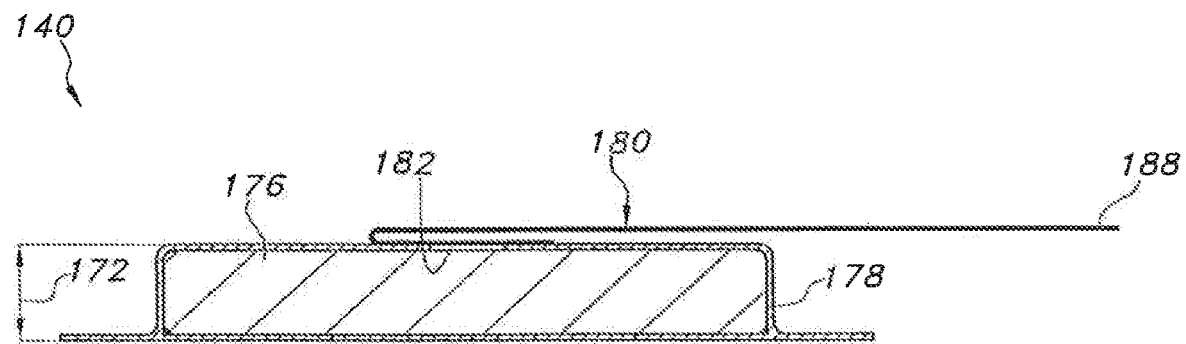
FIG. 9 illustrates a cross-sectional view of a bilateral pushing element of the device shown in FIGS. 5-8, particularly illustrating the bilateral pushing element in an un-actuated or un-expanded position.
Figure 10:
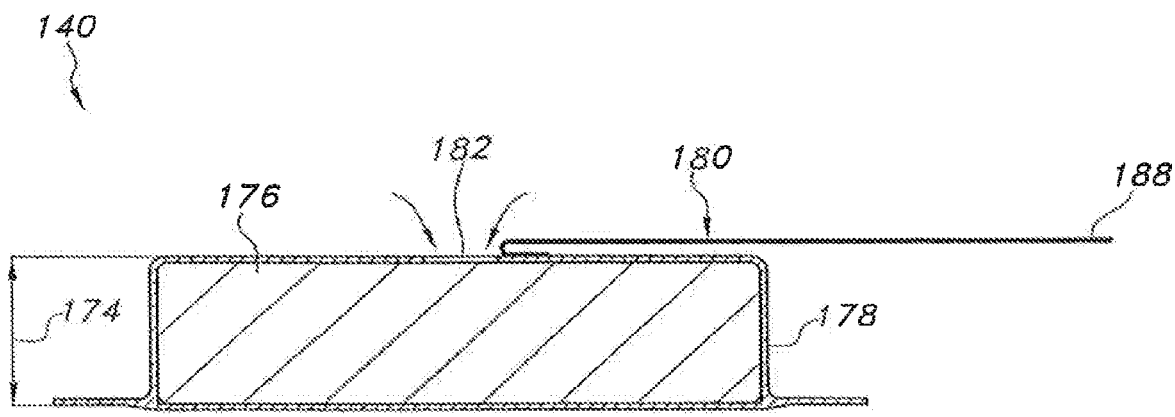
FIG. 10 illustrates another cross-sectional view of the bilateral pushing element of the device shown in FIGS. 5-8, particularly illustrating the bilateral pushing element in an actuated or expanded position.

As particularly shown in FIGS. 9 and 10, in several embodiments, the expandable member may include an expandable material 176 (e.g., compressed foam) vacuum sealed within a suitable outer covering or jacket 178. As such, the expandable member may be activated by releasing the vacuum and allowing air to flow into the jacket 178. For example, as shown in the illustrated embodiment, a peel strip or removable tab 180 may be used to activate the expandable member by exposing a jacket opening 182 defined in the jacket 178. Specifically, as shown in FIG. 9, the removable tab 180 may be initially positioned over the jacket opening 182 so as to seal the opening 182 and maintain the vacuum within the jacket 178. However, as the removable tab 180 is pulled or peeled away from the opening (e.g., by pulling on an exposed end 188 of the tab 109), the seal may be broken and air may flow into the jacket 178, thereby allowing the expandable material 176 contained therein to expand outwardly. In such an embodiment, a portion of the tab 180 may be configured to extend through a corresponding opening or slot 190 defined in the housing 112 to allow the tab 180 to be pulled or peeled away from the opening 182 by the user. It should be appreciated that the jacket 178 may be stretchable, elastic, over-sized and/or may have any other suitable configuration that allows for the expansion of the expandable material 176 contained therein.

In alternative embodiments, the vacuum contained within the jacket 178 may be released using any other suitable activation means. For example, in another embodiment, a push button or other component may be configured to be pressed such that a pin, needle or other penetrating mechanism penetrates the jacket 178, thereby creating an aperture and releasing the vacuum.

Additionally, it should be noted that, since the reservoir 138 is configured as a flexible bladder, the reservoir 138 may be pressurized by the downward force applied by the pushing element 140. As such, the pressure of the drug formulation contained within the reservoir 138 may be increased, thereby facilitating the flow of the formulation from the reservoir 138 to the microneedle assembly 136.

As indicated above, in addition to having a central region 30, 130 and an outer region 32, 132, the disclosed devices 10, 110 may also include intermediate region 34, 134 defined between and separating the central and outer regions 30, 130, 32, 132. In several embodiments, the intermediate regions 34, 134 of the devices 10, 110 may correspond to areas along which the device(s) 10, 110 do not contact the user's skin 18. For example, as shown in FIGS. 2 and 3, the intermediate region 34 of the device 10 may correspond to the open space defined underneath the housing 12 between the adhesive layer 22 and the footprint defined by the microneedle assembly 36, the reservoir 38 and the pushing element 40. Similarly, as shown in FIGS. 6 and 7, the intermediate region 134 of the device 110 may correspond to the open space defined underneath the housing 112 between the adhesive layer 122 and the footprint defined by the microneedle assembly 136 and the pushing element 140. Thus, unlike the central and outer regions wherein forces are transmitted through the microneedle assemblies 36, 136 and adhesive layers 22, 122, respectively, to the user's skin 18, substantially no or no forces may be transmitted through the intermediate regions 34, 134 to the user's skin 18. As such, in several embodiments, a width 192 of the intermediate regions 34, 134 may be selected such that the downward force applied to the skin 18 through central regions 30, 130 and the upward force applied to the skin 18 through the outer regions 32, 132 are sufficiently spaced apart from one another. For example, in one embodiment, the width of the intermediate regions 34, 134 may range from about 0.5 millimeters (mm) to about 15 mm, such as from about 1 mm to about 10 mm or from about 2 mm to about 5 mm and any other subranges therebetween.

The dissociation or functional separation of the lower housing 116 and the microneedle assembly 136 allows the two elements to move independently of one another as well as have transmitted to them substantially opposed components of force. Further, the superimposition of the microneedle assembly 136, pushing element 140 and upper housing 114 allows for the simultaneous application of a continuous upward force to the lower housing 116 (e.g. via the upper housing 114) and a continuous downward force to the microneedle assembly 136. However, it will be appreciated that to effectively allow the independent transmission of these generally opposing forces it will be appreciated that the pushing element 140 and lower housing 116 should also be dissociated or functionally separated from one another.

Additionally, it should be appreciated that, in several embodiments, the configuration of the disclosed pushing elements 40, 140 (e.g., the spring constant of the spring or the expansion constant of the expandable member) may be selected such that the constant force transmitted to the microneedle assemblies 36, 136 is sufficient to cause the microneedles 48 to penetrate the user's skin 18 and remain therein during delivery of the drug formulation. For example, in several embodiments, the pushing elements 40, 140 may be configured such that the upward and downward components of the force applied through the devices 10, 110 ranges from about 0.1 Newtons (N) to about 20 N, such as from about 0.15 N to about 10 N or from about 0.25 N to about 5 N and all other sub ranges therebetween.

It should also be appreciated that, in alternative embodiments of the present subject matter, the pushing element 40, 140 may comprise any other suitable element and/or member capable of providing a continuous bilateral force. For example, in one embodiment, the pushing element 40, 140 may comprise a mechanical actuator, such as a solenoid-activated cylinder or any other suitable actuator, positioned within the housing 12, 112. In a further embodiment, the pushing element 40, 140 may comprise a threaded bolt or screw that is configured to be screwed into the housing 12, 112 so as to mechanically apply the continuous bilateral force through the device 10, 110. Still further, a bladder or other element may be expanded with air pressure such as via a pump or other mechanism.

Moreover, it should be appreciated that the skin attachment means (e.g., adhesive layers 22, 122) may generally be configured to define any suitable width 194 so as to provide a sufficient surface area for transferring the upward component of the force to the user's skin 18. For example, in several embodiments, the width 194 of the skin attachment means may range from about 5 millimeters (mm) to about 30 mm, such as from about 5 mm to about 25 mm or from about 10 mm to about 25 mm and any other subranges therebetween.

As indicated above, the present subject matter is also directed to a method for transdermally delivering a drug formulation. The method may generally include positioning a transdermal drug delivery device 10, 110 adjacent to skin 18 and applying, with a pushing element 40, 140, a continuous bilateral force having a downward component transmitted through a microneedle assembly 36, 136 of the device 10, 110 and an upward component transmitted through skin attachment means 22, 122 of the device 10, 110.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A drug delivery device comprising:
   an outer housing including an upper housing portion and a lower housing portion, the lower housing portion extending from the upper housing portion and having a bottom surface for contacting a user's skin when the drug delivery device is in use;
   the drug delivery device including a central region, an outer region defined by an outer periphery of the lower housing portion at a location at which the drug delivery device contacts the user's skin during use; and an intermediate region extending between and separating the central region and the outer region;
   a microneedle assembly disposed within the central region;
   a reservoir disposed within the central region and above the microneedle assembly, the reservoir containing a drug formulation and being in fluid communication with the microneedle assembly when the drug delivery device is in use;
   a plunger disposed within the central region; and
   a pushing element configured to move the drug delivery device from an un-actuated position to an actuated position,
   wherein in the un-actuated position
   1) the plunger is vertically aligned with and positioned above the reservoir and the microneedle assembly, and
   2) the microneedle assembly is recessed relative to the bottom surface of the lower housing portion and spaced from the user's skin, and
   wherein in the actuated position
   1) the plunger is moved relative to the outer housing by the pushing element to apply a force against the reservoir to thereby move both the reservoir and the microneedle assembly downward such that the microneedle assembly is moved into direct contact with the user's skin, and
   2) the plunger acts on the reservoir, after the microneedle assembly is moved into direct contact with the user's skin, to push the drug formulation from the reservoir to the microneedle assembly.

2. The drug delivery device of claim 1, wherein the reservoir includes a flexible member, and wherein the force applied by the plunger pressurizes the reservoir.

3. The drug delivery device of claim 2, and wherein the force applied by the plunger acts on the drug formulation within the reservoir.

4. The drug delivery device of claim 1, wherein the reservoir is configured as a rigid member containing the drug formulation, and wherein the force applied by the plunger is transmitted through the microneedle assembly without increasing pressure of the drug formulation contained within the reservoir.

5. The drug delivery device of claim 1, wherein the force applied by the plunger is transmitted through the central region to the microneedle assembly, and wherein an opposing force is simultaneously transmitted through the central region to the upper housing portion.

6. The drug delivery device of claim 1, wherein the pushing element comprises a spring compressed between the upper housing portion and the reservoir.

7. The drug delivery device of claim 6, wherein the spring is compressed between the upper housing portion and the plunger.

8. The drug delivery device of claim 1, wherein no force is substantially transmitted through the intermediate region.

9. A drug delivery device comprising:
an upper housing portion attached to a lower housing portion;
a microneedle assembly;
the upper housing portion and the lower housing portion cooperatively defining a cavity and surrounding the microneedle assembly, the drug delivery device being configured such that the lower housing portion is dissociated from the microneedle assembly;
a reservoir disposed within the cavity and being in fluid communication with the microneedle assembly;
a plunger disposed within a central region of the drug delivery device; and
a pushing element configured to move the drug delivery device from an un-actuated position to an actuated position,
wherein in the un-actuated position
1) the plunger is vertically aligned with and positioned above the reservoir and the microneedle assembly, and
2) the microneedle assembly is recessed relative to a bottom surface of the lower housing portion and spaced from a user's skin, and
wherein in the actuated position
1) the plunger is moved relative to the upper housing portion by the pushing element to apply a force against the reservoir to thereby move both the reservoir and the microneedle assembly downward such that the microneedle assembly is moved into direct contact with the user's skin, and
2) the plunger acts on the reservoir, after the microneedle assembly is moved into direct contact with the user's skin, to push a drug formulation from the reservoir to the microneedle assembly.

10. The drug delivery device of claim 9, wherein the reservoir contains the drug formulation, and wherein the force is transmitted through the microneedle assembly without increasing pressure of the drug formulation within the reservoir.

11. The drug delivery device of claim 10, wherein the reservoir is disposed between the microneedle assembly and the pushing element, and wherein the force applied by the plunger is transmitted through the reservoir to the microneedle assembly.

12. The drug delivery device of claim 9, wherein the pushing element comprises, prior to actuation, a compressed member.

13. The drug delivery device of claim 9, wherein the upper housing portion defines an opening, and wherein a top portion of the pushing element extends through the opening, the top portion being movable relative to the upper housing portion, and wherein application of a downward force on the top portion transmits a further downwardly force against the microneedle assembly.

14. The drug delivery device of claim 9, wherein the microneedle assembly, the reservoir, and the pushing element are vertically aligned.

15. A drug delivery device comprising:
a central region, an outer region surrounding the central region, and an intermediate region disposed between the central region and the outer region, the drug delivery device comprising:
a microneedle assembly disposed within the central region of the drug delivery device;
a reservoir disposed within the central region, wherein the reservoir contains a drug formulation, and wherein the reservoir is in selective fluid communication with the microneedle assembly; and
a pushing element disposed above both the reservoir and the microneedle assembly within the central region, the pushing element being configured to provide a force having a downward component to move the microneedle assembly into engagement with a user's skin,
wherein the reservoir is disposed between the microneedle assembly and the pushing element, and wherein the downward component of the force from the pushing element is transmitted through the reservoir to the microneedle assembly without increasing pressure of the drug formulation within the reservoir.

16. The drug delivery device of claim 15, further comprising a housing including an upper housing portion and a lower housing portion, and wherein the microneedle assembly is configured to move independently of the lower housing portion.

17. The drug delivery device of claim 15, further comprising a housing including an upper housing portion and a lower housing portion, and wherein the pushing element comprises a spring compressed between the upper housing portion and the reservoir.

18. The drug delivery device of claim 15, wherein no force is substantially transmitted through the intermediate region.

* * * * *